US012422346B1

(12) United States Patent
Li et al.

(10) Patent No.: US 12,422,346 B1
(45) Date of Patent: Sep. 23, 2025

(54) EXPERIMENTAL APPARATUS AND METHOD FOR INTERFACIAL SHEAR CHARACTERISTIC BETWEEN HYDRATE-BEARING SEDIMENT AND STRUCTURE

(71) Applicant: Dalian University of Technology, Dalian (CN)

(72) Inventors: Yanghui Li, Dalian (CN); Peng Wu, Dalian (CN); Yongchen Song, Dalian (CN); Zhan Huang, Dalian (CN); Mingjun Yang, Dalian (CN); Lei Yang, Dalian (CN); Zheng Ling, Dalian (CN); Lunxiang Zhang, Dalian (CN); Bingbing Chen, Dalian (CN); Zhi Cui, Dalian (CN)

(73) Assignee: Dalian University of Technology, Dalian (CN)

( * ) Notice: Subject to any disclaimer, the term of this patent is extended or adjusted under 35 U.S.C. 154(b) by 0 days.

(21) Appl. No.: 19/194,055

(22) Filed: Apr. 30, 2025

(30) Foreign Application Priority Data

Jul. 9, 2024 (CN) .......................... 202410914110.2

(51) Int. Cl.
*G01N 13/00* (2006.01)
*G01N 3/24* (2006.01)
*G01N 33/24* (2006.01)

(52) U.S. Cl.
CPC ............. *G01N 13/00* (2013.01); *G01N 33/24* (2013.01)

(58) Field of Classification Search
CPC ............ G01N 3/12; G01N 3/24; G01N 13/00; G01N 33/24
See application file for complete search history.

(56) References Cited

U.S. PATENT DOCUMENTS

2023/0033460 A1* 2/2023 Kong ........................ G01N 3/24
2024/0361295 A1* 10/2024 Wei ..................... G01N 33/0016

FOREIGN PATENT DOCUMENTS

| CN | 111896395 A | | 11/2020 | |
| CN | 111982782 A | * | 11/2020 | ........... G01N 23/046 |
| CN | 118746503 A | * | 10/2024 | ............... G01N 3/02 |

OTHER PUBLICATIONS

CN-111982782-A Machine Translation (Year: 2020).*
CN-118746503-A Machine Translation (Year: 2024).*

* cited by examiner

*Primary Examiner* — Nguyen Q. Ha
(74) *Attorney, Agent, or Firm* — Bayramoglu Law Offices LLC (57) ABSTRACT

An experimental apparatus for studying an interfacial shear characteristic between a hydrate-bearing sediment and a structure includes a triaxial shear pressure cell, a torsional and axial loading device, a methane gas source, an upper computer, a first pressure-volume controller, a water bath device, a second pressure-volume controller, an oil tank, a back pressure valve, a gas-water separator, a gas flowmeter, and a data acquisition system, where the triaxial shear pressure cell includes an upper pressing plate, an upper fixed disc, a loading rod, a pressure chamber upper cover, a high-pressure sealing cover, a lower rotating base disc, a thermal insulation plate, a lower pressing plate, a top cap, and a base. The experimental apparatus can achieve in-situ artificial hydrate formation for the study. The multi-directional load control-based shear method supports interfacial shear experiments under a complex stress path, providing hardware support for studying the interfacial shear mechanical characteristic.

14 Claims, 2 Drawing Sheets

EXPERIMENTAL APPARATUS AND METHOD FOR INTERFACIAL SHEAR CHARACTERISTIC BETWEEN HYDRATE-BEARING SEDIMENT AND STRUCTURE

CROSS REFERENCE TO THE RELATED APPLICATIONS

This application is based upon and claims priority to Chinese Patent Application No. 202410914110.2, filed on Jul. 9, 2024, the entire contents of which are incorporated herein by reference.

TECHNICAL FIELD

The present disclosure belongs to the field of fundamental physical property measurement in geotechnical engineering, and specifically relates to an experimental apparatus and method for studying an interfacial shear characteristic between a hydrate-bearing sediment and a well structure.

BACKGROUND

Natural gas hydrates, characterized by high energy density, extensive distribution, and abundant reserves, represent a promising clean energy resource. Due to their low-temperature and high-pressure formation conditions, hydrates primarily exist in deep-sea sub-seafloor layers and terrestrial permafrost zones. The multi-process coupling during hydrate extraction (deformation process, chemical process, seepage process, heat conduction, etc.) will cause phase-change decomposition of the hydrate-bearing sediment at the interface between the sediment and a well structure. This will lead to changes in interfacial mechanical properties between the hydrate-bearing sediment and the well structure, thereby affecting the stability of the well structure and causing safety issues such as wellbore collapse and gas leakage. Therefore, studying the interfacial mechanical characteristic between the hydrate-bearing sediment and the structure holds significant importance for hydrate extraction.

Most existing interfacial shear apparatuses are relatively simple and cannot satisfy the low-temperature and high-pressure conditions for forming the hydrate-bearing sediment. Prior to the present disclosure, Dalian University of Technology (DUT) proposed a parameter measurement apparatus and testing method for soil-structure interface interaction (application Ser. No. 202010806837.0) in 2020. This experimental apparatus has the following shortcomings. 1. It fails to offer the low-temperature and high-pressure conditions for forming the hydrate-bearing sediment, and cannot achieve in-situ formation or maintain stability of the hydrate-bearing sediment. 2. The pressure chamber has insufficient sealing, particularly between the force transmission rod and the pressure chamber, making high-pressure sealing unachievable. 3. The loose connection of the force transmission seat during interfacial shear experiments leads to inaccurate experimental data. 4. The single stress loading method cannot achieve complex stress path shear experiments under the coupling action of vertical load and circumferential torque.

By improving the measurement apparatus and testing method based on existing technical apparatuses, the present disclosure develops a novel experimental apparatus for studying an interfacial shear characteristic between a hydrate-bearing sediment and a structure. The present disclosure can simulate the complex stress state at the interface between the hydrate-bearing sediment and the well structure during hydrate extraction, allowing for further corrections to enhance the accuracy in measuring the mechanical parameter at the sediment-structure interface.

SUMMARY

The present disclosure aims to overcome the defects in the prior art, and provides an experimental apparatus and method for studying an interfacial shear characteristic between a hydrate-bearing sediment and a structure. The present disclosure can accurately measure the interfacial shear mechanical characteristic between a hydrate-bearing sediment and a structure during hydrate extraction, and display results through a data acquisition system, achieving simple operation with a reliable structure.

The present disclosure adopts the following technical solutions.

A first aspect of the present disclosure provides an experimental apparatus for studying an interfacial shear characteristic between a hydrate-bearing sediment and a structure, including a triaxial shear pressure cell, a torsional and axial loading device, a methane gas source, a first pressure-volume controller, a water bath device, a second pressure-volume controller, an oil tank, a back pressure valve, a gas-water separator, a gas flowmeter, and a data acquisition system, where the triaxial shear pressure cell includes a pressure chamber upper cover, a high-pressure sealing cover and a lower rotating base disc that are arranged in sequence from top to bottom to form a sealed pressure chamber; the pressure chamber upper cover and the lower rotating base disc are detachably connected through a plurality of locking lead screws; a water bath jacket communicated with the water bath device is provided around the high-pressure sealing cover; a thermal insulation plate and a lower pressing plate are arranged in sequence below the lower rotating base disc; a top cap, a specimen assembly and a base are coaxially arranged from top to bottom in the pressure chamber; the specimen assembly is clamped by a plurality of fixing screws between the top cap and the base; the base is fixed at a bottom of the pressure chamber, and a cylindrical hole passes through a central-axis position of the base; a loading rod is vertically provided, with a lower part passing through the top cap and the specimen assembly, a bottom extending into the cylindrical hole of the base, and a top protruding from the pressure chamber upper cover and detachably connected to an upper fixed disc; a top of the upper fixed disc is connected to an upper pressing plate; the lower rotating base disc is provided with an exhaust channel, a confining pressure control channel, a temperature sensor channel, an intake channel and a drainage channel that are communicated with the pressure chamber; the exhaust channel is connected to a fourth valve, the back pressure valve, the gas-water separator, and the gas flowmeter in sequence through a tubing; the confining pressure control channel is externally connected to a tubing having a third valve, and a tail end of the tubing is connected to the second pressure-volume controller and the oil tank in parallel; the temperature sensor channel houses a temperature sensor for measuring an internal temperature of the pressure chamber; the intake channel is communicated with the methane gas source through a tubing having a second valve, and the tubing is communicated with the first pressure-volume controller through a branch having a first valve; and the drainage channel communicates the cylindrical hole of the base to an outside; and the torsional and axial loading device includes an axial actuator located at an upper end and fixedly connected to a top of the upper pressing plate and a torsional actuator located at a lower end and fixedly connected to a bottom of the lower pressing plate; the axial actuator, the triaxial shear pressure cell, and the torsional actuator are coaxially arranged; and the data acquisition system is connected to the first pressure-volume controller, the temperature sensor, the second pressure-volume controller, the water bath device, and the torsional and axial loading device.

Preferably, the specimen assembly includes a specimen, filter papers, permeable plates, and a rubber membrane; each of upper and lower ends of the specimen is provided with the filter paper and the permeable plate in sequence from inside to outside; sides of the two permeable plates adjacent to the specimen are respectively provided with ribs for torque transmission; the rubber membrane wraps around the specimen, as well as the filter papers and the permeable plates at the upper and lower ends of the specimen; and two ends of the rubber membrane are fixed to the top cap and the base, respectively.

Furthermore, the two permeable plates are annular, and are bolted to a top of the base and a bottom of the top cap, respectively.

Preferably, a second guide ring and a sealing ring are sleeved in sequence from bottom to top on the bottom of the loading rod, forming a sealed connection between the bottom of the loading rod and the cylindrical hole of the base.

Preferably, the intake channel includes one end passing through the base and communicated with the permeable plate below the specimen and the other end externally connected to the tubing having the second valve; the exhaust channel includes one end passing through the top cap and communicated with the permeable plate above the specimen and the other end externally connected to the tubing having the fourth valve; and the confining pressure control channel includes one end communicated with the pressure chamber and the other end externally connected to the tubing having the third valve, where the tubing splits into two branches: a first branch sequentially connected to a sixth valve and the second pressure-volume controller, and a second branch sequentially connected to a fifth valve and the oil tank.

Preferably, the loading rod is a cylindrical structure as a whole; the top of the loading rod is provided with a protrusion having a square cross-section, and a bottom of the upper fixed disc is provided with a recess having a square cross-section; and the protrusion at the top of the loading rod is inserted into the recess at the bottom of the upper fixed disc, and the protrusion and the recess are connected to each other through a screw.

Preferably, the upper pressing plate, the upper fixed disc, the loading rod, the pressure chamber upper cover, the high-pressure sealing cover, the lower rotating base disc, the thermal insulation plate, the lower pressing plate, the top cap, the specimen assembly, and the base are coaxially arranged; the pressure chamber upper cover, the high-pressure sealing cover, the lower rotating base disc, the thermal insulation plate, the lower pressing plate, the top cap, the specimen assembly, and the base are synchronously rotatable with the loading rod as a central axis while maintaining a sealed state; and the loading rod is slidable vertically in a sealed manner under a constraint of the pressure chamber upper cover, the top cap, the specimen assembly, and the base.

Preferably, the pressure chamber upper cover and the sealing cover are made of aircraft-grade aluminum alloy 7075; the top cap, the base, and the lower rotating base disc are made of 316L stainless steel; the thermal insulation plate is made of polyether ether ketone (PEEK); and the locking lead screws are made of tungsten steel.

Preferably, the loading rod is connected to the pressure chamber upper cover in a sealed manner through a first guide ring.

A second aspect of the present disclosure provides a testing method using the experimental apparatus for studying an interfacial shear characteristic between a hydrate-bearing sediment and a structure according to the first aspect, specifically including:

S1: opening the triaxial shear pressure cell; injecting water into the cylindrical hole of the base through the drainage channel; closing the drainage channel when the sealing ring in the cylindrical hole fully submerges in the water; extending the loading rod into the cylindrical hole; opening the drainage channel, and adjusting a depth of the loading rod extending into the cylindrical hole until the bottom of the loading rod drops below the second guide ring; and closing the drainage channel, allowing water remaining in the cylindrical hole to support the loading rod;

S2: fixing the permeable plates with the ribs to the top of the base and the bottom of the top cap, respectively; placing the filter paper on the permeable plate at the top of the base; sleeving and fixing a bottom of the rubber membrane onto the base; preparing, by a specimen preparation mold, a soil specimen with target water content according to an experimental condition; compacting, by a compaction tool, the soil specimen layer by layer along an axial direction of the loading rod to prepare the specimen; placing the filter paper and the top cap on a top of the specimen; fixing the top cap to the base through the fixing screws to clamp the specimen; sleeving and fixing a top of the rubber membrane onto the top cap; removing the specimen preparation mold, and connecting the exhaust channel; mounting the locking lead screws, the high-pressure sealing cover, and the pressure chamber upper cover in sequence; fixing the locking lead screws with nuts to seal the pressure chamber; and fixing the top of the loading rod to the upper fixed disc;

S3: opening the third valve, as well as the fifth valve for controlling the oil tank; starting a submersible pump in the oil tank, and injecting silicone oil into the pressure chamber through the confining pressure control channel; closing, after the pressure chamber is fully filled with the silicone oil, the fifth valve and the submersible pump; opening the sixth valve for controlling the second pressure-volume controller; controlling, by the second pressure-volume controller, a confining pressure inside the pressure chamber through the confining pressure control channel; adjusting, when a pressure in the second pressure-volume controller rises to 0.2 MPa, the second pressure-volume controller to a constant-pressure mode; opening the first valve, the second valve, and the fourth valve, and adjusting the back pressure valve to a maximum opening; turning on the methane gas source, and delivering methane gas into the first pressure-volume controller and the pressure chamber separately through the tubing; turning off the methane gas source when a pressure in the first pressure-volume controller rises to 0.1 MPa; adjusting the back pressure valve to a minimum opening, and closing the fourth valve; adjusting the first pressure-volume controller and the second pressure-volume controller, controlling a confining pressure increase rate in the pressure chamber to be identical to a pore pressure increase rate, with the confining pressure always maintained 0.1 MPa higher than a pore pressure, until the confining pressure and the pore pressure reach 10.1 MPa and 10 MPa, respectively; activating the water bath device, and adjusting a silicone oil temperature in the pressure chamber to 15° C. to prevent hydrate formation; adjusting the first pressure-volume controller and the second pressure-volume controller to the constant-pressure mode; when a methane gas volume in the first pressure-volume controller ceases to decrease, determining that the specimen is fully gas-saturated; and performing step S4 for in-situ hydrate formation;

S4: adjusting the silicone oil temperature in the pressure chamber to 1° C. through the water bath device, ensuring that a temperature of the specimen is lower than a hydrate phase equilibrium temperature; when the methane gas volume in the first pressure-volume controller exhibits no further significant change, determining that water in a pore of the specimen has fully reacted with the methane gas to form a methane hydrate; and obtaining a consumption of the methane gas in the first pressure-volume controller based on the methane gas volume stabilized in the first pressure-volume controller in the step S3 and the methane gas volume stabilized in the first pressure-volume controller in the step S4, and further calculating a saturation of the methane hydrate;

S5: adjusting and maintaining the pressure of the first pressure-volume controller and the pressure of the second pressure-volume controller according to a specific experimental condition to release an excess pore pressure inside the specimen, thereby achieving consolidation of the sediment specimen; determining that the specimen is fully consolidated when the methane gas volume in the first pressure-volume controller stabilizes; and performing step S6 for interfacial shearing of the specimen; and S6: opening the drainage channel; performing different tests as needed depending on an actual working condition; choosing a control mode for the first pressure-volume controller and the second pressure-volume controller; choosing a torsional shear test or an axial shear test through the torsional and axial loading device, and choosing a single shear or cyclic loading method based on different control loading methods; and acquiring and recording, by the data acquisition system, a stress sensor reading, a torque sensor reading, a torsional angle sensor reading, a displacement sensor reading, and a pore pressure sensor reading during the test, thereby analyzing an impact of hydrate extraction on a mechanical characteristic of a sediment-structure interface.

Compared with the prior art, the present disclosure has the following beneficial effects:

(1) The present disclosure adds a multi-directional load control-based shear method. The upper pressing plate is connected to the axial actuator of the torsional and axial loading device, while the lower pressing plate is connected to the torsional actuator of the torsional and axial loading device. The design achieves coupled axial force and torque loading, realistically simulating the mechanical response characteristic of the interface between the hydrate-bearing sediment and the structure under complex stress states.

(2) The present disclosure innovatively overcomes the drawback of existing contact interface experimental apparatuses being unable to conduct experimental research on the interface between the hydrate-bearing sediment and the structure under high-pressure and low-temperature conditions.

(3) The testing method of the present disclosure features overall simplicity, convenient instrument operation, and precise results, demonstrating strong promotional and practical value for contact interface research experiments. It provides significant reference significance for subsequent studies on contact interface constitutive relationships and numerical simulation parameter calibration.

(4) The split-structure design of the present disclosure ensures that mounting the triaxial pressure chamber after specimen preparation won't disturb or damage the specimen fitted onto the loading rod. In addition, it ensures three-dimensional consolidation of the specimen, thereby ensuring uniform specimen compactness.

Reference Numerals: 1. triaxial shear pressure cell; 2. torsional and axial loading device; 3. methane gas source; 4. upper computer; 5. first pressure-volume controller; 6. water bath device; 7. second pressure-volume controller; 8. oil tank; 9. back pressure valve; 10. gas-water separator; 11. gas flowmeter; 12. data acquisition system; 13a. first valve; 13b. second valve; 13c. third valve; 13d. fourth valve; 13e. fifth valve; 13f. sixth valve; 14. upper pressing plate; 15. upper fixed disc; 16. loading rod; 17. first guide ring; 18. water bath jacket; 19. high-pressure sealing cover; 20. locking screw; 21. top cap; 22. fixing screw; 23. rubber membrane; 24. permeable plate; 25. rib; 26. base; 27. second guide ring; 28. lower rotating base disc; 29. exhaust channel; 30. confining pressure control channel; 31. thermal insulation plate; 32. lower pressing plate; 33. temperature sensor channel; 34. intake channel; 35. drainage channel; 36. pressure chamber upper cover; and 37. specimen.

DETAILED DESCRIPTION OF THE EMBODIMENTS

The present disclosure is described in further detail below with reference to drawings and specific implementations. All the implementations of the present disclosure can be correspondingly combined on the premise that their technical features are not conflicted.

Figure 2:
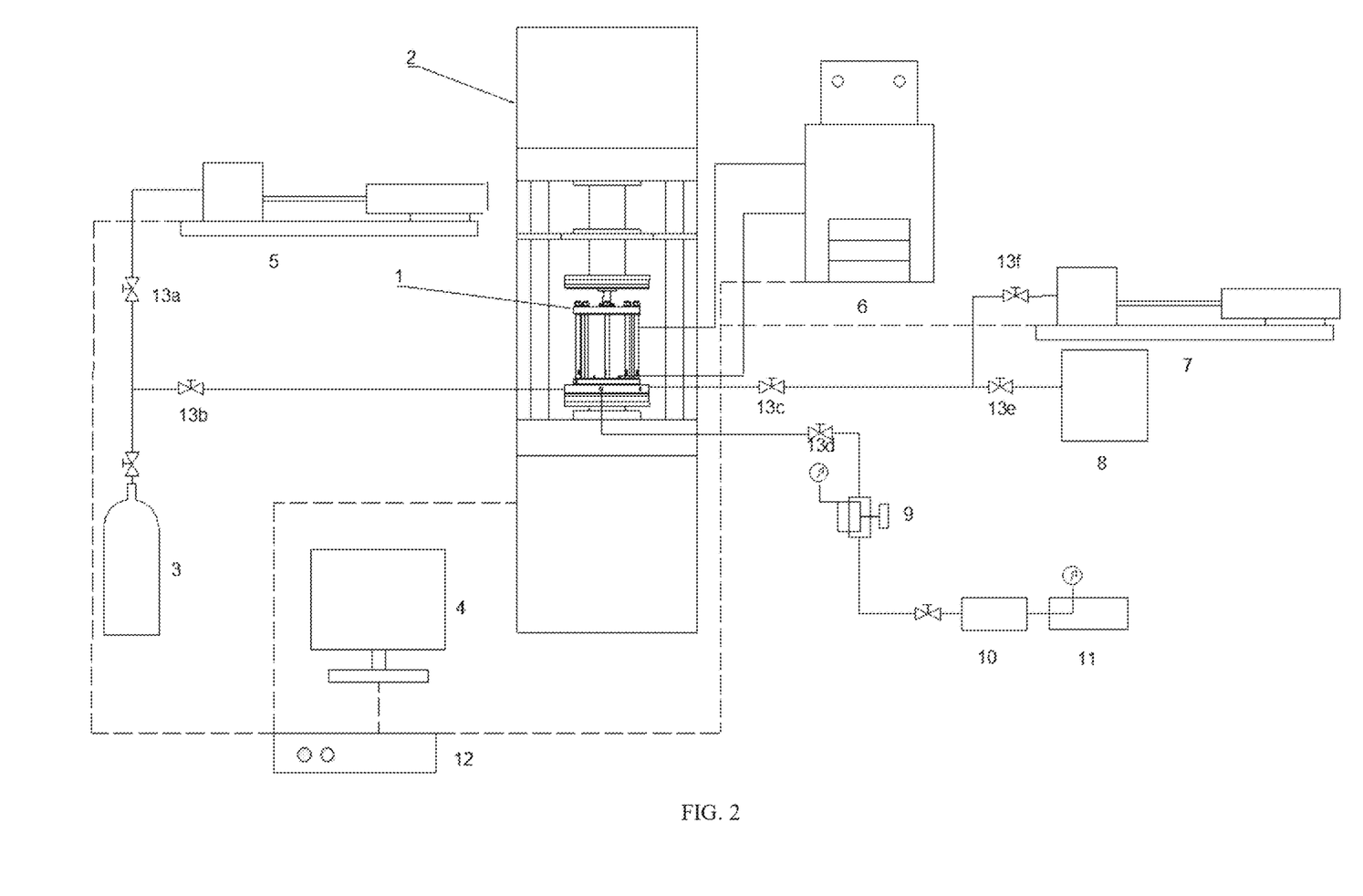
FIG. 2 is an overall systematic diagram of the experimental apparatus for an interfacial shear characteristic between a hydrate-bearing sediment and a structure.

FIG. 2 shows an experimental apparatus for studying an interfacial shear characteristic between a hydrate-bearing sediment and a structure according to the present disclosure. The apparatus mainly includes triaxial shear pressure cell 1, torsional and axial loading device 2, methane gas source 3, first pressure-volume controller 5, water bath device 6, second pressure-volume controller 7, oil tank 8, back pressure valve 9, gas-water separator 10, gas flowmeter 11, and data acquisition system 12.

The structure and connection of each component are specifically described below.

Figure 1:
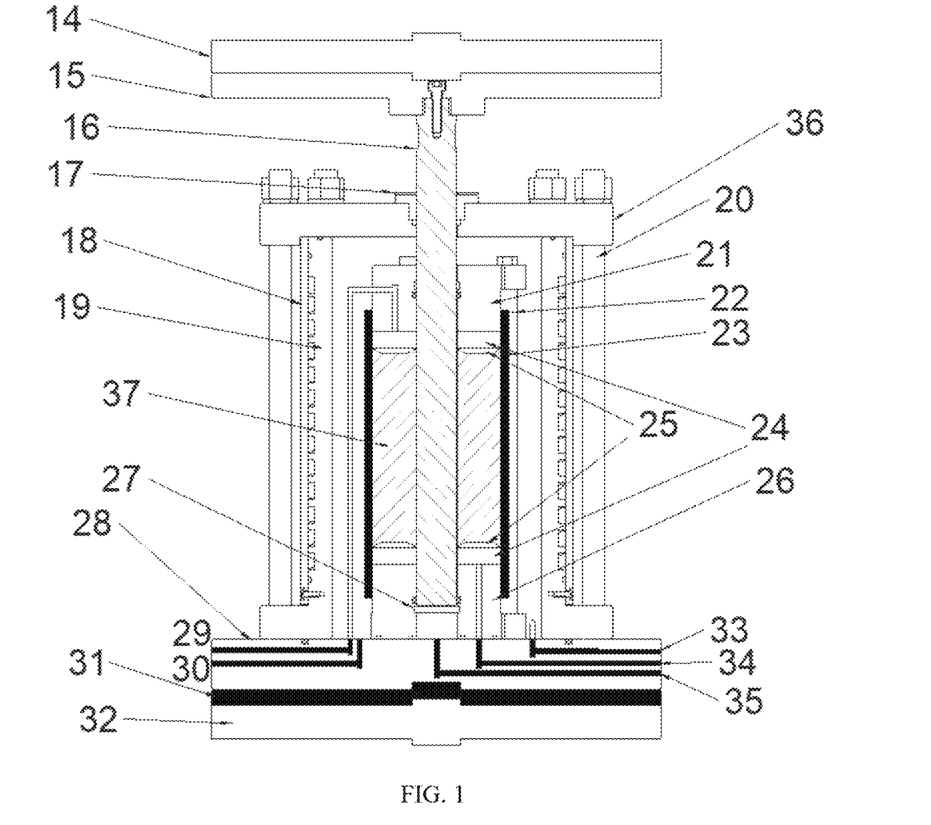
FIG. 1 is a structural diagram of a triaxial shear pressure cell of an experimental apparatus for studying an interfacial shear characteristic between a hydrate-bearing sediment and a structure.

In the present disclosure, as shown in FIG. 1, the triaxial shear pressure cell 1 mainly includes upper pressing plate 14, upper fixed disc 15, loading rod 16, pressure chamber upper cover 36, high-pressure sealing cover 19, lower rotating base disc 28, thermal insulation plate 31, lower pressing plate 32, top cap 21, and base 26. The pressure chamber upper cover 36, the high-pressure sealing cover 19, and the lower rotating base disc 28 are arranged in sequence from top to bottom and detachably connected, forming a sealed pressure chamber. The pressure chamber houses the specimen 37 and enables an interfacial shear characteristic experiment between a hydrate-bearing sediment and a structure. Specifically, two ends of the high-pressure sealing cover 19 are fixed to the pressure chamber upper cover 36 and the lower rotating base disc 28, respectively. Sealing rings are respectively provided between the high-pressure sealing cover 19 and the pressure chamber upper cover 36, and between the high-pressure sealing cover 19 and lower rotating base disc 28. The pressure chamber upper cover 36 and lower rotating base disc 28 are detachably connected through a plurality of locking lead screws 20. The locking lead screws 20 each includes a bottom threaded to the lower rotating base disc 28 and a top fixed to the pressure chamber upper cover 36 through a nut, ensuring tight sealing of the pressure chamber.

In the present disclosure, the triaxial shear pressure cell 1 adopts a split-structure design. The sealing rings achieve sealing between the pressure chamber upper cover 36 and the high-pressure sealing cover 19, as well as between the lower rotating base disc 28 and the high-pressure sealing cover 19. The pressure chamber upper cover 36 and the lower rotating base disc 28 are connected and fixed through the locking lead screws 20. Designing the high-pressure sealing cover 19 and the pressure chamber upper cover 36 as two split components facilitates subsequent connection between the upper cover 36 and the loading rod 16 without damaging the specimen 37.

In the present disclosure, as shown in FIG. 1, water bath jacket 18 is coaxially sleeved around the high-pressure sealing cover 19. The water bath jacket 18 includes a water inlet and a water outlet. The water inlet and the water outlet are communicated through a tubing with an outlet end and an inlet end of the water bath device 6, forming a circulation loop. The water bath device 6 regulates temperature inside the pressure chamber. In practical use, the water bath jacket 18 and the high-pressure sealing cover 19 are connected in a sealed manner through a sealing ring, and the water bath jacket 18 is fixed to an outer surface of the high-pressure sealing cover 19 through a bolt. The water bath jacket 18 is made of a material with good thermal insulation performance and features an internal spiral pattern to enhance heat exchange efficiency and reduce thermal loss.

In the present disclosure, as shown in FIG. 1, the thermal insulation plate 31 is connected below the lower rotating base disc 28, and the lower pressing plate 32 is connected below the thermal insulation plate 31. The top cap 21, a specimen assembly and the base 26 are coaxially arranged from top to bottom in the pressure chamber. The specimen assembly is clamped by a plurality of fixing screws 22 between the top cap 21 and the base 26. Specifically, each of the fixing screws 22 includes a threaded bottom and an unthreaded top. The bottom of the fixing screw 22 is threaded to the base 26. The top cap 21 achieves circumferential fixation through the fixing screws 22, so the top cap 21 is vertically movable during specimen consolidation, thereby achieving three-dimensional compaction. In other words, to prevent torsional deformation of the specimen 37 during a torsion shear experiment, the top cap 21 above the specimen 37 and the base 26 below the specimen are fixed by the fixing screws 22. The top cap 21 is vertically movable, ensuring that the specimen 37 can undergo three-dimensional consolidation.

In the present disclosure, as shown in FIG. 1, the base 26 is fixed at a bottom of the pressure chamber, and a cylindrical hole passes through a central-axis position of the base. The loading rod 16 is vertically provided, with a lower part passing through the top cap 21 and the specimen assembly in sequence and a bottom extending into the cylindrical hole of the base 26. The bottom of the loading rod 16 and the cylindrical hole of the base 26 are connected in a sealed manner through a sealing ring, and a connection between the loading rod 16 and the top cap 21 is sealed through a sealing ring. The design prevents confining pressure silicone oil from leaking into the specimen 37 during a subsequent experimental stage, thereby eliminating potential contamination of the specimen. In practical use, second guide ring 27 and a sealing ring are sleeved from bottom to top on the bottom of the loading rod 16, forming a sealed connection between the bottom of the loading rod and an inner wall of the cylindrical hole of the base 26 through the sealing ring and the second guide ring 27. A top of the loading rod 16 partially protrudes from the pressure chamber upper cover 36 and is detachably connected to the upper fixed disc 15. The upper fixed disc 15 is connected to the upper pressing plate 14. A connection between the loading rod 16 and the pressure chamber upper cover 36 remains sealed. In practical use, the loading rod 16 can be designed as a solid steel cylindrical structure with two smooth ends and a rough middle section. The top of the loading rod is provided with a protrusion having a square cross-section, and a bottom of the upper fixed disc 15 is provided with a recess having a square cross-section. The protrusion at the top of the loading rod 16 is inserted into the recess at the bottom of the upper fixed disc 15, and the protrusion and the recess are screwed to ensure stability of the loading rod 16 during the experiment. The square top design of the loading rod 16 maximizes rotational inertia to prevent damage of the loading rod 16 during a torsion experiment. In practical use, the loading rod 16 is connected to the pressure chamber upper cover 36 in a sealed manner through the first guide ring 17. In other words, to minimize friction between the loading rod 16 and the triaxial shear pressure cell 1 during the experiment, upper and lower ends of the loading rod 16 are respectively provided with the first guide ring 17 and the second guide ring 27.

In a preferred embodiment of the present disclosure, the specimen assembly mainly includes the specimen 37, filter papers, permeable plates 24, and rubber membrane 23. Each of upper and lower ends of the specimen 37 is provided with the filter paper and the permeable plate 24 in sequence from inside to outside. Sides of the two permeable plates 24 adjacent to the specimen 37 are respectively provided with ribs 25 for torque transmission. The ribs 25 are embedded into the specimen 37 during the experiment. The rubber membrane 23 wraps around the specimen 37, as well as the filter papers and the permeable plates 24 at the upper and lower ends of the specimen. Two ends of the rubber membrane 23 are fixed to the top cap 21 and the base 26, respectively. In practical use, the two permeable plates 24 are annular, and are bolted to the top of the base 26 and the bottom of the top cap 21, respectively.

In the present disclosure, as shown in FIGS. 1 and 2, the lower rotating base disc 28 is provided with exhaust channel 29, confining pressure control channel 30, temperature sensor channel 33, intake channel 34 and drainage channel 35 that are communicated with the pressure chamber. The exhaust channel 29 is connected to fourth valve 13*d*, the back pressure valve 9, the gas-water separator 10, and the gas flowmeter 11 in sequence through a tubing. The confining pressure control channel 30 is externally connected to a tubing having third valve 13*c*, and a tail end of the tubing is connected to the second pressure-volume controller 7 and the oil tank 8 in parallel. The temperature sensor channel 33 houses a temperature sensor for measuring an internal temperature of the pressure chamber. The intake channel 34 is communicated with the methane gas source 3 through a tubing having second valve 13*b*, and the tubing is communicated with the first pressure-volume controller 5 through a branch having first valve 13a. The drainage channel 35 communicates the cylindrical hole of the base 26 to an outside.

Specifically, the exhaust channel 29 includes one end passing through the top cap 21 and communicated with the permeable plate 24 above the specimen 37 and the other end passing through the lower rotating base disc 28 and externally connected to the tubing having the fourth valve 13d. In practical use, to facilitate structural assembly, the exhaust channel 29 is divided into three tubing sections, which are arranged along an exhaust direction inside the top cap 21, the pressure chamber, and the lower rotating base disc 28, respectively. The tubing in the top cap 21 and the lower rotating base disc 28 may be implemented via drilled holes, whereas the tubing inside the pressure chamber may adopt a flexible hose made of polytetrafluoroethylene (PTFE). The confining pressure control channel 30 includes one end communicated with the pressure chamber and the other end externally connected to the tubing having the third valve 13c. The tubing splits into two branches: a first branch sequentially connected to sixth valve 13f and the second pressure-volume controller 7, and a second branch sequentially connected to fifth valve 13e and the oil tank 8. The temperature sensor channel 33 includes one end communicated with the pressure chamber and the other end communicated with the outside. A temperature sensor is placed through this channel, with its probe located inside the pressure chamber, thereby measuring temperature data within the pressure chamber. The intake channel 34 includes one end passing through the base 26 and communicated with the permeable plate 24 below the specimen 37 and the other end externally connected to the tubing having the second valve 13b. The drainage channel 35 includes one end communicated with the cylindrical hole in the base 26 and the other end communicated with the outside, serving to inject or drain water into/from the pressure chamber.

In the present disclosure, as shown in FIG. 2, the torsional and axial loading device 2 adopts a device structure from the prior art. It includes an axial actuator at an upper end, a torsional actuator at a lower end, as well as a force and torque sensor (for recording a stress sensor reading and a torque sensor reading), a displacement sensor, a torsional angle sensor, etc. The specific structure is not redundantly described herein. The axial actuator at the upper end of the torsional and axial loading device 2 is fixedly connected to a top of the upper pressing plate 14, while the torsional actuator at the lower end is fixedly connected to a bottom of the lower pressing plate 32. The axial actuator, the triaxial shear pressure cell 1, and the torsional actuator are coaxially arranged. The data acquisition system 12 is connected to the first pressure-volume controller 5, the temperature sensor, the second pressure-volume controller 7, the water bath device 6, and the torsional and axial loading device 2. The data acquisition system 12 may be connected to upper computer 4 to display data in real time.

In a preferred embodiment of the present disclosure, to ensure better transmission effects, the upper pressing plate 14, the upper fixed disc 15, the loading rod 16, the pressure chamber upper cover 36, the high-pressure sealing cover 19, the lower rotating base disc 28, the thermal insulation plate 31, the lower pressing plate 32, the top cap 21, the specimen assembly, and the base 26 are coaxially arranged. The pressure chamber upper cover 36, the high-pressure sealing cover 19, the lower rotating base disc 28, the thermal insulation plate 31, the lower pressing plate 32, the top cap 21, the specimen assembly, and the base 26 are synchronously rotatable with the loading rod 16 as a central axis while maintaining a sealed state. The loading rod 16 is slidable vertically in a sealed manner under a constraint of the pressure chamber upper cover 36, the top cap 21, the specimen assembly, and the base 26.

In a preferred embodiment of the present disclosure, the pressure chamber upper cover 36 and the sealing cover 19 may be made of aircraft-grade aluminum alloy 7075, treated with a hard anodization anti-corrosion method. The aircraft-grade aluminum alloy 7075 has high strength and thermal conductivity, enabling resistance to high pressure and improved heat exchange efficiency. The top cap 21, the base 26, and the lower rotating base disc 28 may be made of 316L stainless steel. To reduce thermal loss during experiments, the thermal insulation plate 31 is provided at a bottom of the lower rotating base disc 28. The thermal insulation plate 31 may be made of rigid materials with excellent thermal insulation properties, such as polyether ether ketone (PEEK). The locking lead screws 20 may be made of tungsten steel, which has high strength and hardness, to fix the sealing cover 19 and the pressure chamber upper cover 36, ensuring that the pressure chamber can withstand high pressure.

Based on the above experimental apparatus for an interfacial shear characteristic between a hydrate-bearing sediment and a structure, the present disclosure further provides a testing method, including the following steps.

Before an experiment, it is confirmed whether all tubing in the apparatus are properly connected according to FIG. 2. Specifically:

A water bath channel on the water bath jacket 18 is connected to the water bath device 6 through a flexible tubing (e.g., a rubber hose) to achieve temperature control in the pressure chamber. The confining pressure control channel 30 is connected to the second pressure-volume controller 7 and the oil tank 8 through pressure-resistant tubing (e.g., steel pipes) via the third valve 13c, the fifth valve 13e, and the sixth valve 13f to control confining pressure on the sediment specimen. The intake channel 34 is connected to the first pressure-volume controller 5 and the methane gas source 3 through pressure-resistant tubing via the first valve 13a and the second valve 13b to regulate pore pressure in the sediment specimen. The methane gas source supplies gas for in-situ hydrate formation of the sediment specimen. The exhaust channel 29 is connected to the back pressure valve 9, the gas-water separator 10, and the gas flowmeter 11 through pressure-resistant tubing via the fourth valve 13d to control back pressure in the sediment specimen. The gas flowmeter 11 is configured to calculate a hydrate saturation change of the sediment specimen during a decomposition experiment. The temperature sensor in the temperature sensor channel 33, the first pressure-volume controller 5, the second pressure-volume controller 7, the torsional and axial loading device 2, and the water bath device 6 are connected to the data acquisition system 12 to acquire data during an experimental process of the experimental apparatus for an interfacial shear characteristic between a hydrate-bearing sediment and a structure.

After it is confirmed that all the tubing are properly connected, the following operations are performed sequentially.

S1. Loading rod mounting:

The triaxial shear pressure cell 1 is opened, while maintaining connections among the lower pressing plate 32, the thermal insulation plate 31, the lower rotating base disc 28, and the base 26. Deionized water is injected into the cylindrical hole of the base 26 through the drainage channel 35. The drainage channel 35 is closed when the sealing ring in the cylindrical hole fully submerges in the water. The loading rod 16 extends into the cylindrical hole. The drainage channel 35 is opened, and a depth of the loading rod 16 extending into the cylindrical hole is adjusted until the bottom of the loading rod 16 drops below the second guide ring 27. The drainage channel 35 is closed, allowing water remaining in the cylindrical hole to support the loading rod 16.

During subsequent formal experiment, the loading rod will press downward, so there is a certain distance between the bottom end of the loading rod and the base. However, to prevent the loading rod from moving downward under gravity, the water is used to support the loading rod. During subsequent specimen preparation, the soil specimen and the loading rod form an integrated structure with increased weight. Therefore, this operation also prevents the loading rod from damaging the integrated structure under gravity.

S2. Specimen preparation and mounting:

The permeable plates 24 with the ribs 25 are fixed to the top of the base 26 and the bottom of the top cap 21, respectively. The filter paper is placed on the permeable plate 24 at the top of the base 26. A bottom of the rubber membrane 23 is sleeved and fixed onto the base 26. A specimen preparation mold is placed on the base, and the other section of the rubber membrane is fixed to an upper end of the mold. A vacuum pump adsorbs the rubber membrane onto the specimen preparation mold. The soil specimen with target water content is prepared according to an experimental condition. Along an axial direction of the loading rod 16, the soil specimen is compacted layer by layer by a compaction tool to prepare the specimen 37. After the preparation, the filter paper and the top cap 21 are placed on the top of the specimen 37. The top cap 21 is fixed to the base 26 through the fixing screws 22 to clamp the specimen 37. A top of the rubber membrane 23 is sleeved and fixed onto the top cap 21. The specimen preparation mold is removed, and the exhaust channel 29 is connected. Subsequently, the locking lead screws 20, the high-pressure sealing cover 19, and the pressure chamber upper cover 36 are mounted sequentially. The locking lead screws 20 are fixed with nuts to seal the pressure chamber. Finally, the top of the loading rod 16 is fixed to the upper fixed disc 15.

S3. Specimen saturation:

The third valve 13c, as well as the fifth valve 13e for controlling the oil tank 8, is controlled. A submersible pump in the oil tank 8 is started, and silicone oil is injected into the pressure chamber through the confining pressure control channel 30. After the pressure chamber is fully filled with the silicone oil, the fifth valve 13e and the submersible pump are closed. The sixth valve 13f for controlling the second pressure-volume controller 7 is opened. The second pressure-volume controller 7 controls a confining pressure inside the pressure chamber through the confining pressure control channel 30. When a pressure in the second pressure-volume controller 7 rises to 0.2 MPa, the second pressure-volume controller 7 is adjusted to a constant-pressure mode. The first valve 13a, the second valve 13b, and the fourth valve 13d are opened, and the back pressure valve 9 is adjusted to a maximum opening. The methane gas source 3 is turned on, and methane gas is delivered into the first pressure-volume controller 5 and the pressure chamber separately through the tubing. When a pressure in the first pressure-volume controller 5 rises to 0.1 MPa, the methane gas source 3 is turned off. The back pressure valve 9 is adjusted to a minimum opening, and the fourth valve 13d is closed. The first pressure-volume controller 5 and the second pressure-volume controller 7 are adjusted to control a confining pressure increase rate in the pressure chamber to be identical to a pore pressure increase rate, with the confining pressure always maintained 0.1 MPa higher than a pore pressure, until the confining pressure and the pore pressure reach 10.1 MPa and 10 MPa, respectively. The water bath device 6 is activated, and a silicone oil temperature in the pressure chamber is adjusted to 15° C. to prevent hydrate formation. The first pressure-volume controller 5 and the second pressure-volume controller 7 are adjusted to the constant-pressure mode. When a methane gas volume in the first pressure-volume controller 5 ceases to decrease, the specimen 37 is deemed fully gas-saturated, and S4 is performed for in-situ hydrate formation.

During this process, the silicone oil temperature in the pressure chamber is acquired through the temperature sensor.

S4. In-situ hydrate formation:

The silicone oil temperature in the pressure chamber is adjusted to 1° C. through the water bath device 6, ensuring that a temperature of the specimen 37 is lower than a hydrate phase equilibrium temperature. When the methane gas volume in the first pressure-volume controller 5 exhibits no further significant change, it indicates that the water in a pore of the specimen 37 has fully reacted with the methane gas to form a methane hydrate. Based on the methane gas volume stabilized in the first pressure-volume controller 5 in the step S3 and the methane gas volume stabilized in the first pressure-volume controller 5 in the step S4, a consumption of the methane gas in the first pressure-volume controller 5 is obtained, and further a saturation of the methane hydrate is calculated.

S5. Specimen consolidation:

The pressure of the first pressure-volume controller 5 and the pressure of the second pressure-volume controller 7 are adjusted and maintained according to a specific experimental condition to release an excess pore pressure inside the specimen 37, thereby achieving consolidation of the sediment specimen. When the methane gas volume in the first pressure-volume controller 5 stabilizes, the specimen 37 is deemed fully consolidated. Step S6 is performed for interfacial shearing of the specimen 37.

S6. Specimen shearing:

The drainage channel 35 is opened. Depending on an actual working condition, different tests are performed as needed. A control mode for the first pressure-volume controller 5 and the second pressure-volume controller 7 are chosen. A torsional shear test or an axial shear test is chosen through the torsional and axial loading device 2, and a single shear or cyclic loading method is chosen based on different control loading methods. An instrument control system employs two control methods: stress control method and strain control method. The stress control method is used to regulate a stress increment rate, while the strain control method is used to regulate a displacement change rate. The two control methods both allow different loading rates as needed. The test can be manually stopped or automatically stopped based on a predefined failure criterion. During the test, the data acquisition system 12 acquires and records a stress sensor reading, a torque sensor reading, a torsional angle sensor reading, a displacement sensor reading, and a pore pressure sensor reading. These data are used to analyze the impact of hydrate extraction on an interfacial mechanical characteristic between the sediment and the structure.

Specifically, when a torsional or axial shear experiment is performed, the torsional rotating base disc 28 drives the sealing cover 19, the base 26, the specimen 37, the top cap 21, and the pressure chamber upper cover 36 to rotate synchronously. The upper fixed disc 15 drives the loading rod 16 to move axially, enabling the shear experiment at an interface between the specimen and the loading rod.

The present disclosure features a simple structure and convenient operation, and can achieve in-situ hydrate formation. The multi-directional load control-based shear method supports interfacial shear experiments under a complex stress path, providing hardware support for studying the interfacial mechanical characteristic between a hydrate-bearing sediment and a structure.

The above described are merely preferred embodiments of the present disclosure, and are not intended to limit the present disclosure. Various changes and transformations can be made by persons of ordinary skill in the relevant technical field without departing from the spirit and scope of the present disclosure. All technical solutions obtained by means of equivalent substitution or equivalent transformation should fall within the protection scope of the present disclosure.

The invention claimed is:

1. An experimental apparatus for studying an interfacial shear characteristic between a hydrate-bearing sediment and a structure, the apparatus comprising a triaxial shear pressure cell, a torsional and axial loading device, a methane gas source, a first pressure-volume controller, a water bath device, a second pressure-volume controller, an oil tank, a back pressure valve, a gas-water separator, a gas flowmeter, and a data acquisition system, wherein the triaxial shear pressure cell comprises a pressure chamber upper cover, a high-pressure sealing cover and a lower rotating base disc, wherein the pressure chamber upper cover, the high-pressure sealing cover and the lower rotating base disc are arranged in sequence from top to bottom to form a sealed pressure chamber; the pressure chamber upper cover and the lower rotating base disc are detachably connected through a plurality of locking lead screws; a water bath jacket communicated with the water bath device is provided around the high-pressure sealing cover; a thermal insulation plate and a lower pressing plate are arranged in sequence below the lower rotating base disc; a top cap, a specimen assembly and a base are coaxially arranged from top to bottom in the sealed pressure chamber; the specimen assembly is clamped by a plurality of fixing screws between the top cap and the base; the base is fixed at a bottom of the sealed pressure chamber, and a cylindrical hole passes through a central-axis position of the base; a loading rod is vertically provided, with a lower part passing through the top cap and the specimen assembly, a bottom extending into the cylindrical hole of the base, and a top protruding from the pressure chamber upper cover and detachably connected to an upper fixed disc; a top of the upper fixed disc is connected to an upper pressing plate; the lower rotating base disc is provided with an exhaust channel, a confining pressure control channel, a temperature sensor channel, an intake channel and a drainage channel, wherein the exhaust channel, the confining pressure control channel, the temperature sensor channel, the intake channel and the drainage channel are communicated with the sealed pressure chamber; the exhaust channel is connected to a fourth valve, the back pressure valve, the gas-water separator, and the gas flowmeter in sequence through a first tubing; the confining pressure control channel is externally connected to a second tubing having a third valve, and a tail end of the second tubing is connected to the second pressure-volume controller and the oil tank in parallel; the temperature sensor channel houses a temperature sensor for measuring an internal temperature of the sealed pressure chamber; the intake channel is communicated with the methane gas source through a third tubing having a second valve, and the third tubing is communicated with the first pressure-volume controller through a branch having a first valve; and the drainage channel communicates the cylindrical hole of the base to an outside; and the torsional and axial loading device comprises an axial actuator located at an upper end and fixedly connected to a top of the upper pressing plate and a torsional actuator located at a lower end and fixedly connected to a bottom of the lower pressing plate; the axial actuator, the triaxial shear pressure cell, and the torsional actuator are coaxially arranged; and the data acquisition system is connected to the first pressure-volume controller, the temperature sensor, the second pressure-volume controller, the water bath device, and the torsional and axial loading device.

2. The experimental apparatus for studying an interfacial shear characteristic between a hydrate-bearing sediment and a structure according to claim 1, wherein the specimen assembly comprises a specimen, filter papers, two permeable plates, and a rubber membrane; each of upper and lower ends of the specimen is provided with the filter paper and the permeable plate in sequence from inside to outside; sides of the two permeable plates adjacent to the specimen are respectively provided with ribs for torque transmission; the rubber membrane wraps around the specimen and the filter papers and the two permeable plates at the upper and lower ends of the specimen; and two ends of the rubber membrane are fixed to the top cap and the base, respectively.

3. The experimental apparatus for studying an interfacial shear characteristic between a hydrate-bearing sediment and a structure according to claim 2, wherein the two permeable plates are annular, and are bolted to a top of the base and a bottom of the top cap, respectively.

4. The experimental apparatus for studying an interfacial shear characteristic between a hydrate-bearing sediment and a structure according to claim 1, wherein a second guide ring and a sealing ring are sleeved in sequence from bottom to top on the bottom of the loading rod, forming a sealed connection between the bottom of the loading rod and the cylindrical hole of the base.

5. The experimental apparatus for studying an interfacial shear characteristic between a hydrate-bearing sediment and a structure according to claim 2, wherein the intake channel comprises a first end passing through the base and communicated with the permeable plate below the specimen and a second end externally connected to the third tubing having the second valve; the exhaust channel comprises a first end passing through the top cap and communicated with the permeable plate above the specimen and a second end externally connected to the first tubing having the fourth valve; and the confining pressure control channel comprises a first end communicated with the sealed pressure chamber and a second end externally connected to the second tubing having the third valve, wherein the second tubing splits into a first branche-branch and a second branch, wherein the first branch is sequentially connected to a sixth valve and the second pressure-volume controller, and the second branch is sequentially connected to a fifth valve and the oil tank.

6. The experimental apparatus for studying an interfacial shear characteristic between a hydrate-bearing sediment and a structure according to claim 5, wherein the loading rod is a cylindrical structure as a whole; the top of the loading rod is provided with a protrusion having a square cross-section, and a bottom of the upper fixed disc is provided with a recess having a square cross-section; and the protrusion at the top of the loading rod is inserted into the recess at the bottom of the upper fixed disc, and the protrusion and the recess are connected to each other through a screw.

7. The experimental apparatus for studying an interfacial shear characteristic between a hydrate-bearing sediment and a structure according to claim 5, wherein the upper pressing plate, the upper fixed disc, the loading rod, the pressure chamber upper cover, the high-pressure sealing cover, the lower rotating base disc, the thermal insulation plate, the lower pressing plate, the top cap, the specimen assembly, and the base are coaxially arranged; the pressure chamber upper cover, the high-pressure sealing cover, the lower rotating base disc, the thermal insulation plate, the lower pressing plate, the top cap, the specimen assembly, and the base are synchronously rotatable with the loading rod as a central axis while maintaining a sealed state; and the loading rod is slidable vertically in a sealed manner under a constraint of the pressure chamber upper cover, the top cap, the specimen assembly, and the base.

8. The experimental apparatus for studying an interfacial shear characteristic between a hydrate-bearing sediment and a structure according to claim 5, wherein the pressure chamber upper cover and the high-pressure sealing cover are made of aircraft-grade aluminum alloy 7075; the top cap, the base, and the lower rotating base disc are made of 316L stainless steel; the thermal insulation plate is made of polyether ether ketone (PEEK); and the locking lead screws are made of tungsten steel.

9. The experimental apparatus for studying an interfacial shear characteristic between a hydrate-bearing sediment and a structure according to claim 5, wherein the loading rod is connected to the pressure chamber upper cover in a sealed manner through a first guide ring.

10. A testing method using the experimental apparatus for studying an interfacial shear characteristic between a hydrate-bearing sediment and a structure according to claim 5, the method comprising:

S1: opening the triaxial shear pressure cell; injecting water into the cylindrical hole of the base through the drainage channel; closing the drainage channel when the sealing ring in the cylindrical hole fully submerges in the water; extending the loading rod into the cylindrical hole; opening the drainage channel, and adjusting a depth of the loading rod extending into the cylindrical hole until the bottom of the loading rod drops below the second guide ring; and closing the drainage channel, allowing water remaining in the cylindrical hole to support the loading rod;

S2: fixing the two permeable plates with the ribs to the top of the base and the bottom of the top cap, respectively; placing the filter paper on the permeable plate at the top of the base; sleeving and fixing a bottom of the rubber membrane onto the base; preparing, by a specimen preparation mold, a soil specimen with target water content according to an experimental condition; compacting, by a compaction tool, the soil specimen layer by layer along an axial direction of the loading rod to prepare the specimen; placing the filter paper and the top cap on a top of the specimen; fixing the top cap to the base through the fixing screws to clamp the specimen; sleeving and fixing a top of the rubber membrane onto the top cap; removing the specimen preparation mold, and connecting the exhaust channel; mounting the locking lead screws, the high-pressure sealing cover, and the pressure chamber upper cover in sequence; fixing the locking lead screws with nuts to seal the sealed pressure chamber; and fixing the top of the loading rod to the upper fixed disc;

S3: opening the third valve, and opening the fifth valve for controlling the oil tank; starting a submersible pump in the oil tank, and injecting silicone oil into the sealed pressure chamber through the confining pressure control channel; closing, after the sealed pressure chamber is fully filled with the silicone oil, the fifth valve and the submersible pump; opening the sixth valve for controlling the second pressure-volume controller; controlling, by the second pressure-volume controller, a confining pressure inside the sealed pressure chamber through the confining pressure control channel; adjusting, when a pressure in the second pressure-volume controller rises to 0.2 MPa, the second pressure-volume controller to a constant-pressure mode; opening the first valve, the second valve, and the fourth valve, and adjusting the back pressure valve to a maximum opening; turning on the methane gas source, and delivering methane gas into the first pressure-volume controller and the sealed pressure chamber separately through the third tubing; turning off the methane gas source when a pressure in the first pressure-volume controller rises to 0.1 MPa; adjusting the back pressure valve to a minimum opening, and closing the fourth valve; adjusting the first pressure-volume controller and the second pressure-volume controller, controlling a confining pressure increase rate in the sealed pressure chamber to be identical to a pore pressure increase rate, with the confining pressure always maintained 0.1 MPa higher than a pore pressure, until the confining pressure and the pore pressure reach 10.1 MPa and 10 MPa, respectively; activating the water bath device, and adjusting a silicone oil temperature in the sealed pressure chamber to 15° C. to prevent hydrate formation; adjusting the first pressure-volume controller and the second pressure-volume controller to the constant-pressure mode; when a methane gas volume in the first pressure-volume controller ceases to decrease, determining that the specimen is fully gas-saturated; and performing step S4 for in-situ hydrate formation;

S4: adjusting the silicone oil temperature in the sealed pressure chamber to 1° C. through the water bath device, ensuring that a temperature of the specimen is lower than a hydrate phase equilibrium temperature; when the methane gas volume in the first pressure-volume controller exhibits no further significant change, determining that water in a pore of the specimen has fully reacted with the methane gas to form a methane hydrate; and obtaining a consumption of the methane gas in the first pressure-volume controller based on the methane gas volume stabilized in the first pressure-volume controller in the step S3 and the methane gas volume stabilized in the first pressure-volume controller in the step S4, and further calculating a saturation of the methane hydrate;

S5: adjusting and maintaining the pressure of the first pressure-volume controller and the pressure of the second pressure-volume controller according to a specific experimental condition to release an excess pore pressure inside the specimen, thereby achieving consolidation of the sediment specimen; determining that the specimen is fully consolidated when the methane gas volume in the first pressure-volume controller stabilizes; and performing step S6 for interfacial shearing of the specimen; and S6: opening the drainage channel; performing different tests as needed depending on an actual working condition; choosing a control mode for the first pressure-volume controller and the second pressure-volume controller; choosing a torsional shear test or an axial shear test through the torsional and axial loading device, and choosing a single shear or cyclic loading method based on different control loading methods; and acquiring and recording, by the data acquisition system, a stress sensor reading, a torque sensor reading, a torsional angle sensor reading, a displacement sensor reading, and a pore pressure sensor reading during the torsional shear test or the axial shear test, thereby analyzing an impact of hydrate extraction on a mechanical characteristic of a sediment-structure interface.

11. The testing method according to claim 10, wherein in the experimental apparatus for the studying an interfacial shear characteristic between a hydrate-bearing sediment and a structure, the loading rod is a cylindrical structure as a whole; the top of the loading rod is provided with a protrusion having a square cross-section, and a bottom of the upper fixed disc is provided with a recess having a square cross-section; and the protrusion at the top of the loading rod is inserted into the recess at the bottom of the upper fixed disc, and the protrusion and the recess are connected to each other through a screw.

12. The testing method according to claim 10, wherein in the experimental apparatus for studying an interfacial shear characteristic between a hydrate-bearing sediment and a structure, the upper pressing plate, the upper fixed disc, the loading rod, the pressure chamber upper cover, the high-pressure sealing cover, the lower rotating base disc, the thermal insulation plate, the lower pressing plate, the top cap, the specimen assembly, and the base are coaxially arranged; the pressure chamber upper cover, the high-pressure sealing cover, the lower rotating base disc, the thermal insulation plate, the lower pressing plate, the top cap, the specimen assembly, and the base are synchronously rotatable with the loading rod as a central axis while maintaining a sealed state; and the loading rod is slidable vertically in a sealed manner under a constraint of the pressure chamber upper cover, the top cap, the specimen assembly, and the base.

13. The testing method according to claim 10, wherein in the experimental apparatus for studying an interfacial shear characteristic between a hydrate-bearing sediment and a structure, the pressure chamber upper cover and the high-pressure sealing cover are made of aircraft-grade aluminum alloy 7075; the top cap, the base, and the lower rotating base disc are made of 316L stainless steel; the thermal insulation plate is made of polyether ether ketone (PEEK); and the locking lead screws are made of tungsten steel.

14. The testing method according to claim 10, wherein in the experimental apparatus for studying an interfacial shear characteristic between a hydrate-bearing sediment and a structure, the loading rod is connected to the pressure chamber upper cover in a sealed manner through a first guide ring.

* * * * *